United States Patent [19]

Klicek

[11] Patent Number: 5,281,216
[45] Date of Patent: Jan. 25, 1994

[54] ELECTROSURGICAL BIPOLAR TREATING APPARATUS

[75] Inventor: Michael S. Klicek, Boulder, Colo.

[73] Assignee: Valleylab, Inc., Boulder, Colo.

[21] Appl. No.: 860,816

[22] Filed: Mar. 31, 1992

[51] Int. Cl.$^5$ ............................................. A61B 17/39
[52] U.S. Cl. ....................................... 606/42; 606/48; 606/50
[58] Field of Search ...................... 606/42, 48, 50, 51

[56] References Cited

U.S. PATENT DOCUMENTS

| | | | |
|---|---|---|---|
| 4,043,342 | 8/1977 | Morrison, Jr. | 606/48 |
| 4,074,718 | 2/1978 | Morrison, Jr. | 606/48 X |
| 4,228,800 | 10/1980 | Degler, Jr. et al. | 606/48 |
| 4,706,667 | 11/1987 | Roos | 606/48 |
| 5,013,312 | 5/1991 | Parins et al. | 606/50 X |

*Primary Examiner*—Lee S. Cohen
*Attorney, Agent, or Firm*—Peter C. Richardson; Lawrence C. Akers; Mark Dryer

[57] ABSTRACT

An electrosurgical bipolar treating apparatus comprising a handpiece to which is connected a first active electrode and a second return electrode having exposed distal ends which define a bipolar tip for electrosurgically treating tissue at an operational site on a patient, which tip is structured so that both distal ends simultaneously contact said tissue and wherein the active electrode has a higher tissue to electrode impedance than the return electrode.

3 Claims, 1 Drawing Sheet

ELECTROSURGICAL BIPOLAR TREATING APPARATUS

BACKGROUND OF THE INVENTION

This invention relates to an electrosurgical apparatus for treating tissue and, more particularly, to an electrosurgical bipolar treating apparatus.

The use of electrosurgery for cutting tissue is known in the art. A typical electrosurgical cutting apparatus comprises a handpiece having an active monopolar electrode which conveys high frequency electrical energy from a generator to tissue at an operational site. The electric circuit is completed through a return electrode attached to the patient.

A monopolar electrosurgical device gives satisfactory performance as long as the circuit is efficiently completed through the return electrode. However, because of possible dangers of electrical current flowing through the patient's body in undefined paths as it is conducted to the return electrode, there has been a growing demand for a bipolar cutting device. A bipolar device is defined as a device which has two electrodes in close proximity to each other as well as to the surgical site and which does not require a patient return electrode for the performance of safe and efficacious electrosurgery.

In a bipolar device, one of the electrodes is defined as the active electrode and the other as the return electrode. The active electrode must be capable of setting up a steam barrier with the tissue and be capable of performing the same operations of cut, blend and coag as a monopolar device. As used herein the term "treating" means the operations of cut, bland and coag.

The return electrode must be capable of returning the current delivered by the active electrode with minimal to no tissue desiccation or destruction at its contact point with the patient's tissue.

Although bipolar instruments are known in the prior art, heretofore manufacturers have focused attention on the generator output stage of units used with monopolar devices and a satisfactory and safe bipolar treating device has not been produced.

It has now been found that a safe and efficacious bipolar treating electrosurgical apparatus is obtained by suitably controlling the configuration and characteristics of the bipolar electrodes.

SUMMARY OF THE INVENTION

According to the present invention there is provided an electrosurgical bipolar treating apparatus comprising a handpiece adapted to be connected to a generator which provides high frequency electrical energy for performing an electrosurgical operation, which handpiece has mounted thereon a first active electrode having a proximal end and a distal end and a second return electrode having a proximal end and a distal end, the proximal end of each electrode being connected to the handpiece and the distal end of each electrode being exposed and being close to but spaced apart from the distal end of the other electrode, said exposed distal ends defining a bipolar tip for electrosurgically treating tissue at an operational site on a patient, which tip is structured so that both distal ends simultaneously contact said tissue and wherein the exposed distal end of the active electrode is substantially the same size as the exposed distal end of the return electrode and the exposed distal end of the active electrode is coated with a high impedance material so that the active electrode has a higher tissue to electrode impedance than the return electrode.

As described above, to accomplish bipolar treating one of the electrodes of the apparatus must have a substantially larger tissue to electrode impedance than the other. As defined herein, the electrode having the higher tissue contact impedance is the active electrode and the electrode with low tissue contact impedance is the return electrode. Different techniques may be used to achieve the required differentiation of tissue contact impedance between the two electrodes, as described hereinafter.

In a preferred embodiment of the apparatus, the exposed distal end of the return electrode is associated with spring means in the form of a compressible fluid to provide an intimate pressure contact with tissue when the apparatus is used.

In a modified embodiment of the apparatus the exposed distal end of the return electrode has a substantially greater tissue contact area than the exposed distal end of the active electrode and the exposed distal end of the return electrode is associated with a compressible fluid to provide an intimate pressure contact with tissue when the apparatus is used. If desired, the exposed distal end of the active electrode may be coated with a high impedance material.

Embodiments of the invention may include switching means on the handpiece for activating the generator in the cut, blend and coag modalities. The cut and blend activation may be achieved by a single means of keying where the modality delivered is defined by the generator configuration.

The apparatus also may include capability for drip irrigation, with possible flow control, to keep the tissue moist during surgery.

Additionally, the apparatus may include suction means for aspiration of eschar and tissue debris.

Switching means for activation of the above capabilities may be incorporated in the handpiece.

BRIEF DESCRIPTION OF THE DRAWINGS

Preferred embodiments of the invention are illustrated in the accompanying drawings, in which.

DETAILED DESCRIPTION OF THE INVENTION

Figure 1:
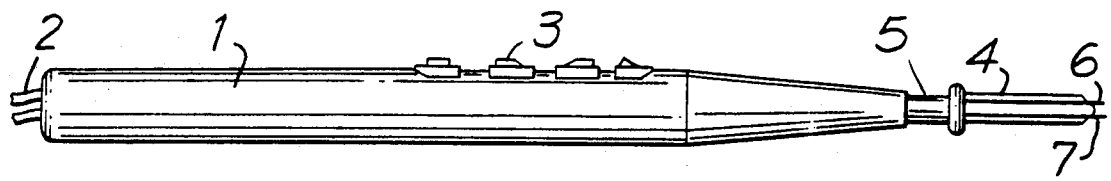
FIG. 1 is a schematic side elevation of a standard electrosurgical pencil having a disposable bipolar electrode connected thereto.

The apparatus illustrated in FIG. 1 of the accompanying drawings includes a standard electrosurgical pencil comprising a handpiece 1 adapted to be connected to an electrosurgical generator through cables 2 and having a switch module 3 for activating the various modalities of the apparatus. The embodiment illustrated shows four switches, but the handpiece may contain any number of switches, depending upon the capabilities desired. For example, in addition to the cut capability according to the invention, the apparatus may include the capabilities of coag, blend, aspiration (suction) and-/or irrigation. Circuitry for the selection and activation of these capabilities is known in the art and is not described in detail herein.

A disposable bipolar electrode 4 is connected to the handpiece through a releasable connector 5. The bipolar electrode comprises an active electrode with an exposed distal end 6 and a return electrode with an exposed distal end 7. The exposed distal ends 6, 7 define a tip for bipolar cutting, which tip is shown in more detail in FIG. 2.

Figure 2:
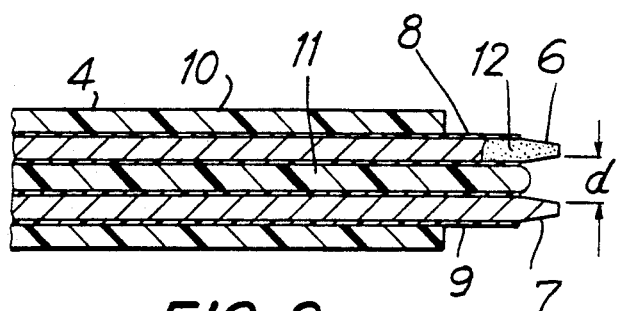
FIG. 2 is an enlarged side view, partly in section, of a bipolar electrode according to the invention.
Figure 2A:
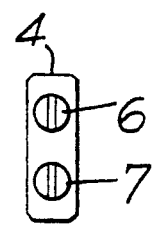
FIG. 2A is an end view of the distal end of the bipolar electrode of FIG. 2.

The bipolar electrode 4 illustrated in detail in FIG. 2 comprises an active electrode with an exposed distal end 6 and a return electrode with an exposed distal end 7. The active electrode and return electrode shown in the embodiment of FIG. 2 are of the type known in the art as "needle" electrodes and are made of an electrically conducting metal, for example, stainless steel. Typical needle electrodes have a diameter of about 0.5 mm. Apart from the exposed distal ends these needle electrodes are individually enveloped in a thin sleeve of electrically-insulating material 8, 9, such as a polyalkylene or silicone rubber. The complete bipolar unit 4 is enveloped in a sleeve 10 of electrically-insulating material.

The active needle electrode and the return needle electrode are mounted in side-by-side relationship spaced apart by a high voltage resistant dielectric 11. The dielectric material may be a plastic, such as polypropylene, or a ceramic.

The exposed distal end 6 of the active electrode is coated with a high impedance material 12 such as a carboniferous material. The differential between the impedance of the active electrode and that of the return is optimized to provide the desired cutting effect and preferably it is at least two-fold.

The distal end of the active electrode and the distal end of the return electrode define a tip for bipolar electrosurgical cutting and the distance d between the distal ends is minimized so that open circuit voltage does not spark through the air gap between the electrodes. Using needle electrodes as described above, the distance d is of the order of 1 mm.

According to the invention, it is essential that the distal ends 6, 7 of the electrodes simultaneously contact tissue during operation of the apparatus.

Figure 3:
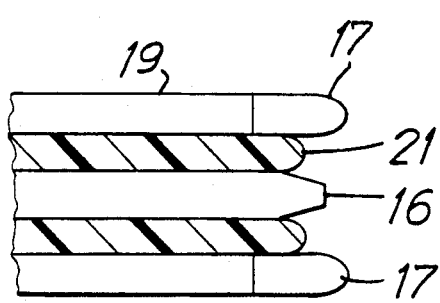
FIG. 3 is a side view, partly in section, of another embodiment of a bipolar electrode according to the invention.

FIG. 3 illustrates an alternative embodiment of the invention wherein the exposed distal end 17 of the return electrode is an annular ring spaced apart from the exposed distal end 16 of an axially disposed active electrode by a concentric ring 21 of high voltage resistant dielectric material.

Figure 3A:
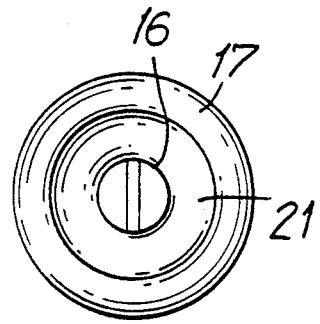
FIG. 3A is a view of the distal end of the electrode of FIG. 3.

FIG. 3A is an end view of this embodiment.

The return electrode, apart from the exposed distal end, is individually insulated with a sleeve 19 of electrically-insulating material. The active electrode is similarly insulated (not shown).

Figure 3B:
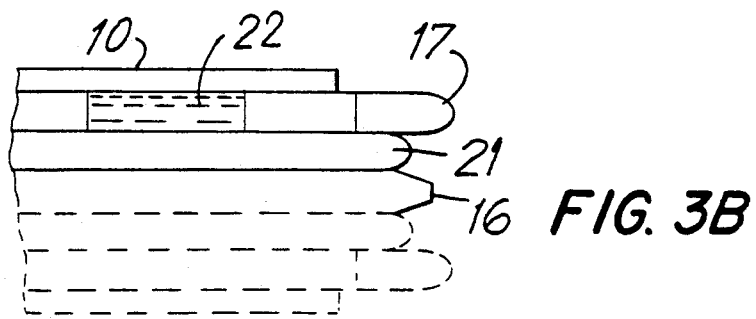
FIG. 3B is a side view, partially cut-away, of another aspect of the embodiment of FIG. 3.

The complete bipolar electrode is insulated with a sleeve 10 of insulating material as shown in FIG. 3B.

To ensure simultaneous contact of both the active and return electrodes with tissue during operation of the apparatus the distal end of the return electrode is associated with spring means in the form of a compressible fluid 22 located in the annular ring. This compressible fluid maintains the annular distal end of the return electrode clear relative to the distal end of the active electrode when the apparatus is not in use but enables the distal end of the return electrode to be pushed back toward the proximal end of the handpiece so as to provide an intimate pressure contact with tissue when the apparatus is used.

In this embodiment the distal end 16 of the active electrode may or may not be coated with a high impedance coating, depending upon achievement of the required impedance differential for optimum performance.

Providing the essential characteristics of impedance differential and simultaneous tissue contact are achieved, numerous variations in the specific configuration of the bipolar electrode are possible within the scope of the invention.

By adhering to the stated characteristics, safe and efficient bipolar electrosurgical cutting is achieved.

I claim:

1. An electrosurgical bipolar treating apparatus comprising a handpiece adapted to be connected to a generator which provides high frequency electrical energy for performing an electrosurgical operation, which handpiece has mounted thereon a first active electrode having a proximal end and a distal end and a second return electrode having a proximal end and a distal end, the proximal end of each electrode being connected to the handpiece and the distal end of each electrode being exposed and being close to but spaced apart from the distal end of the other electrode, said exposed distal ends defining a bipolar tip for electrosurgically treating tissue at an operational site on a patient, which tip is structured so that both distal ends simultaneously contact said tissue and wherein the exposed distal end of the active electrode is substantially the same size as the exposed distal end of the return electrode and the exposed distal end of the active electrode is coated with a high impedance material so that the active electrode has a higher tissue to electrode impedance than the return electrode.

2. An apparatus according to claim 1 which includes hand-operated switching means mounted on the handpiece for activating said electrodes.

3. An apparatus according to claim 2, in which the electrosurgical operation includes blend and coag and said switching means also includes switches for activating the generator in the blend and coag modalities.

* * * * *